United States Patent [19]

White

[11] 4,028,379

[45] June 7, 1977

[54] PROCESS FOR PREPARING 2-AMINO-2-ALKYLTHIO-1-NITROETHYLENE COMPOUNDS

[75] Inventor: George Raymond White, Harpenden, England

[73] Assignee: Smith Kline & French Laboratories Limited, Welwyn Garden City, England

[22] Filed: May 5, 1976

[21] Appl. No.: 683,355

[30] Foreign Application Priority Data

May 15, 1975 United Kingdom ............ 20628/75

[52] U.S. Cl. .................. 260/309; 260/294.8 G; 260/306.8 R; 260/306.8 D; 260/306.8 A; 260/307 R; 260/307 H; 260/308 R; 260/308 A; 260/583 EE; 260/583 F; 260/583 DD

[51] Int. Cl.² ...................................... C07D 233/64

[58] Field of Search ..... 260/309, 294.8 G, 306.8 R, 260/306.8 D, 306.8 A, 307 R, 307 H, 308 R, 308 A, 583 EE, 583 DD, 583 F

[56] References Cited

UNITED STATES PATENTS

| 3,876,647 | 4/1975 | Durant et al. .............. 260/294.8 G |
| 3,953,460 | 4/1976 | Durant et al. .............. 260/294.8 G |

FOREIGN PATENTS OR APPLICATIONS 1,398,426  6/1975  United Kingdom ............... 260/309

Primary Examiner—Natalie Trousof
Attorney, Agent, or Firm—Joan S. Keps; Richard D. Foggio; William H. Edgerton

[57] ABSTRACT

A process for preparing 2-amino-2-alkylthio-1-nitroethylene compounds by reacting a 1-lower alkylsulfinyl-1-lower alkylthio-2-nitroethylene with an amine. The products of the process are intermediates for the production of histamine $H_2$-antagonists.

4 Claims, No Drawings

PROCESS FOR PREPARING 2-AMINO-2-ALKYLTHIO-1-NITROETHYLENE COMPOUNDS

This invention relates to an improved process for the synthesis of amino compounds, in particular 2-amino-2-alkylthio-1-nitroethylenes and to the compounds so produced. Such a process is particularly useful for the production of certain compounds which are intermediates for the production of histamine $H_2$-antagonists. A step in the process presently available for the production of many of these compounds involves the displacement of an alkylthio e.g., a methylthio group by an amino group and in certain cases, for example where the amine is not very reactive, this displacement may not take place easily. It is an object of the present invention to increase the efficiency of such displacement reactions.

According to the present invention we therefore provide a process wherein a compound of the Formula I:

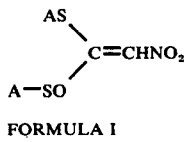

FORMULA I wherein A is lower alkyl is reacted with an amine of Formula II:

$R_1NH_2$

FORMULA II wherein $R_1$ is lower alkyl, lower alkoxy, 2,2,2-trifluoroethyl, $(CH_2)_nR_2$ or $HetCH_2Z(CH_2)_2$; Het is an imidazole, thiazole, pyridine, isothiazole, oxazole, isoxazole, triazole or thiadiazole ring, which ring is optionally substituted by lower alkyl, hydroxyl, lower alkoxy, chlorine or bromine; Z is sulphur or methylene; n is an integer from 1 to 12; and $R_2$ is hydroxy, lower alkoxy or lower alkylamino.

The compounds produced by the process of the present invention i.e., compounds of Formula III;

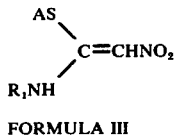

FORMULA III are intermediates for the production of histamine $H_2$-antagonists and may be converted to an $H_2$-antagonist compound of Formula IV:

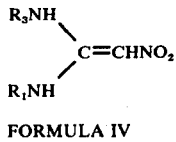

FORMULA IV by reaction thereof with an amine of formula $R_3NH_2$ wherein $R_3$ is lower alkyl, lower alkoxy, 2,2,2-trifluoroethyl, $(CH_2)_nR_2$ or $HetCH_2Z(CH_2)_2$ but with the proviso that if $R_1$ is not $HetCH_2Z(CH_2)_2$ then $R_3$ must be $HetCH_2Z(CH_2)_2$.

Throughout the present specification, by the term "lower alkyl" we mean an alkyl group containing from 1 to 4 carbon atoms.

The process of the present invention, when carried out between equivalent amounts of the compounds of formulae I and II results in the production of the compound of Formula III without the formation of any significant amounts of the bis compound of Formula V:

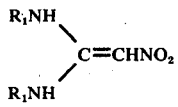

FORMULA V and this selectivity may be certain cases be desirable. The process of the invention may, in general, be carried out under mild conditions. For example gradual addition of a solution of the amine of Formula II to a stirred solution of the compound of Formula I at a temperature of from 15°–40° C normally results in the production of the required compound of Formula III which may then be isolated from the reaction mixture and purified by conventional methods. The reaction has been found to proceed successfully even when using amines which are normally comparatively unreactive e.g., those of Formula II wherein R is alkoxy or 2,2,2-trifluoroethyl.

The compound of Formula I may be produced by treatment of the corresponding compound of Formula VI:

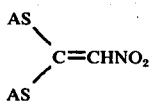

FORMULA VI wherein A has the above significance with an oxidizing agent such as hydrogen peroxide. This reaction may be carried out in a suitable solvent such as acetic acid.

In the process of our invention A is most conveniently methyl. The process is particularly useful for the production of compounds of Formula III wherein $R_1$ is alkoxy, $(CH_2)_n R_2$ or Het $CH_2Z(CH_2)_2$.

Those compounds wherein $R_1$ is $HetCH_2Z(CH_2)_2$ are particularly preferred when Het is an imidazole, thiazole or pyridine ring optionally substituted by methyl, hydroxy or chlorine. Specific compounds which may be conveniently prepared by the process of the present invention include:

a. 1-nitro-2-methylthio-2-methylaminoethylene
b. 1-nitro-2-methylthio-2-ethylaminoethylene
c. 1-nitro-2-methylthio-2-(2,2,2-trifluoroethylamino)ethylene
d. 1-nitro-2-methylthio-2-methoxyaminoethylene
e. 1-nitro-2-methylthio-2-[2-((5-methyl-4-imidazolyl)methylthio)ethylamino]ethylene
f. 1-nitro-2-methylthio-2-[2-((2-thiazolyl)methylthio)ethylamino]ethylene
g. 1-nitro-2-methylthio-2-[4-(2-thiazolyl)butylamino]ethylene Compounds (a) to (g) above, which are all intermediates for $H_2$-antagonists, may be reacted with a suitable amine to yield $H_2$-antagonist compounds such as:

a. 1-nitro-2-methylamino-2-[2-((5-methyl-4-imidazolyl)methylthio)ethylamino]ethylene
b. 1-nitro-2-ethylamino-2-[2-((5-methyl-4-imidazolyl)methylthio)ethylamino]ethylene
c. 1-nitro-2-(2,2,2-trifluoroethylamino)-2-[2-((5-methyl-4-imidazolyl)methylthio)ethylamino]ethylene
d. 1-nitro-2-methoxyamino-2-[2-((5-methyl-4-imidazolyl)methylthio)ethylamino]ethylene
e. 1-nitro-2,2-bis-[2-((5-methyl-4-imidazolyl)methylthio)ethylamino]ethylene
f. 1-nitro-2-methylamino-2-((2-thiazolyl)methylthio)ethylamino]ethylene
g. 1-nitro-2-methylamino-2-[4-(2-thiazolyl)butylamino]ethylene.

The $H_2$-antagonists of Formula IV act at histamine $H_2$-receptors which as described by Black et al. (Nature, 1972, 236, 385) may be defined as those histamine receptors which are not blocked by "antihistamines" such as mepyramine but are blocked by burimamide. Blockade of histamine $H_2$-receptors is of utility in inhibiting the biological actions of histamine which are not inhibited by antihistamines. Histamine $H_2$-antagonists are useful, for example, as inhibitors of gastric acid secretion.

It will be understood that the compounds of Formula I and III to VI, may exist as two distinct geometrical isomers i.e., in the "Z" and "E" forms. Unless specifically stated to the contrary any reference to such a compound is intended to refer to the Z and E forms individually as well as to mixtures of the two forms.

The invention is illustrated but in no way limited by the following Examples 2–11. Example 1 shows the preparation of a starting material.

EXAMPLE 1

1-Methylsulphinyl-1-methylthio-2-nitroethylene

To a stirred solution in acetic acid (4,500 ml) of 1,1-bismethylthio-2-nitroethylene (165 g) at 60° was added over 15 minutes 30% (100 volume) hydrogen peroxide (113 ml) and the reaction mixture maintained, with stirring, at 60° for 17 hours. Evaporation of the solvent under reduced pressure gave a residue which was taken up in methylethylketone, reevaporated and finally crystallised from methylethylketone to yield the title product as a yellow solid m.p. 137°–143°. Further purification yielded the pure Z and E isomers. One of these had m.p. 145°–148° and from the mother liquors the other isomer was obtained after further working up and recrystallisation from methylal, m.p. 90–93°.

Found: C, 26.7; H, 3.9; N, 7.7; S, 35.1% $C_4H_7NO_3S_2$. Requires: C, 26.5; H, 3.9; N, 7.7; S, 35.4%.

EXAMPLE 2

1-Methylthio-1-methylamino-2-nitroethylene

A solution in methanol (100 ml) of methylamine (9.4 g) was added dropwise over 10 minutes to a stirred solution in methanol (500 ml) at 25°–30° of 1-methylsulphinyl-1-methylthio-2-nitroethylene (18.1 g). T.L.C. analysis indicated immediate complete disappearance of the sulphoxide. Evaporation of the reaction mixture yielded an oily solid which, on recrystallisation from isopropanol gave the title product (8.1 g) m.p. 113°–113.5°

Found: C, 32.4; H, 5.4; N, 18.9; S, 21.6% $C_4H_8N_2S$. Requires: C, 32.4; H, 5.5; N, 18.8; S, 21.8%.

EXAMPLE 3

1-Methylthio-1-ethylamino-2-nitroethylene

A solution in methanol (5ml) of ethylamine (225 mg) was added dropwise over 2 minutes to a stirred solution in methanol (30 ml) at 32° of 1-methylsulphinyl-1-methylthio-2-nitroethylene (906 mg). Evaporation of the reaction mixture gave an oil which was crystallised from ispropanol to give the title product (230 mg) m.p. 66°–67.5°.

Found: C, 36.8; H, 6.2; N, 17.0% $C_5H_{10}N_2O_2S$. Requires: C, 37.0; H, 6.2; N, 17.3%.

EXAMPLE 4

1-Methylthio-1-[4-(2-thiazolyl)butylamino]-2-nitroethylene

A solution of 2-(4-aminobutyl)thiazole (1.56 g) in methanol (35 ml) was added dropwise over 30 minutes to a stirred solution of 1-methylsulphinyl-1-nitroethylene (1.81 g) in methanol (60ml). The product was isolated as in the previous Examples and recrystallised from isopropanol to give the title product, m.p. 75.5°–76°.

Found: C, 43.8; H, 5.5; N, 15.1; S, 23.0% $C_{10}H_{15}N_3O_2S_2$. Requires: C, 43.9; H, 5.5; N, 15.4; S, 23.4%.

EXAMPLE 5

1-Methylthio-1-(2,2,2-trifluoroethylamino)-2-nitroethylene

A solution of 2,2,2-trifluoroethylamine )4.0 g) in methanol (45 ml) was added dropwise to a suspension of 1-methylsulphinyl-1-methylthio-2-nitroethylene (3.6 g) in methanol(150 ml) at 20° for 24 hours. Evaporation of the reaction mixture and recrystallisation from either gave the title compound as a pale orange crystalline solid m.p. 101°–102°.

Found: C, 28.0 H, 3.2 N, 12.9: S, 15.1%. $C_5H_7F_3N_2O_2S$. Requires: C, 27.8 H, 3.3: N, 13.0 : S, 14.8%.

EXAMPLE 6

1-Nitro-2-methylthio-2-[2-((5-methyl-4-imidazolyl)methylthio)ethylamino]ethylene A solution of 2-[(5-methyl-4-imidazolyl)methylthio]ethylamine (8.56 g) in methanol (115 ml) was added dropwise over 13 minutes to a stirred solution of 1-methylsulphinyl-1-methylthio-2-nitroethylene (9.06 g) in methanol (150 ml) at 40°. Evaporation of the reaction mixture and recrystallisation of the resultant solid from isopropanol yielded the title product (7.15 g), m.p. 147°–150°.

Found: C, 41.7; H, 5.6; N, 19.1; S, 21.7% $C_{10}H_{16}N_4O_2S_2$. Requires: C, 41.6; H, 5.6; N, 19.4; S, 22.2%.

EXAMPLE 7

1-Nitro-2-methylthio-2-[(2-thiazolylmethylthio)ethylamine]ethylene

An aqueous solution (25 ml) of 2-(2-thiazolylmethylthio)ethylamine (1.74 g) was added dropwise over 10 minutes to a stirred solution in methanol (60 ml) at 35° of 1-methylsulphinyl-1-methylthio-2-nitroethylene (1.81 g). Cooling to −5° yielded a solid product which on recrystallisation from isopropanol gave the title product (1.63 g) m.p. 90°–92°.

Found: C, 37.3; H, 4.5; N, 14.5; S, 32.7% $C_9H_{13}N_3O_2S_3$. Requires: C, 37.1; H, 4.5; N, 14.4; S, 33.0%.

EXAMPLE 8

1-Nitro-2-methylthio-2-[2-((3-methoxy--2-pyridyl)methylthio)ethylamino]ethylene

A solution of 2-[2-aminoethylthiomethyl]-3-methoxypyridine (2.1 g) in methanol (33 ml) was added over 25 minutes to a stirred solution of 1-methylthio-1-methylsulphinyl-2-nitroethylene (2.1 g) in methanol (75 ml) at 30°. After standing for an hour the solution was concentrated to give a yellow-brown oil which was crystallised from ethanol/ether to yield 1-nitro-2-methylthio-2-[2-((3-methoxy-2-pyridyl)methylthio)ethylamino]ethylene (1.9 g), m.p. 87.5°–88.5°.

Found: C, 45.5; H, 5.4; N, 13.3% $C_{12}H_{17}N_3O_3S_2$. Requires: C, 45.7; H, 5.4; N, 13.3%.

EXAMPLE 9

Reaction in the procedure of Example 2 of 1-methylsulphinyl-1-methylthio-2-nitroethylene with the following amines:

methoxyamine
  4-aminobutanol
  2-methoxyethylamine and
  2-methylaminoethylamine yielded the following products respectively:

1-nitro-2-methoxyamino-2-methylthioethylene,
  1-nitro-2-(4-hydroxybutyl)amino-2-methylthioethylene,
  1-nitro-2-(2-methoxyethyl)amino-2-methylthioethylene and
  1-nitro-2-(2-methylaminoethyl)amino-2-methylthioethylene.

EXAMPLE 10

Reaction in the procedure of Example 2 of 1-methylsulphinyl-1-methylthio-2-nitroethylene with the following compounds:

a. 3-chloro-2-[(2-aminoethyl)thiomethyl]pyridine,
b. 3-bromo-2-[(2-aminoethyl)thiomethyl]pyridine,
c. 3-hydroxy-2-[(2-aminoethyl)thiomethyl]pyridine,
d. 3-[(2-aminoethyl)thiomethyl]isothiazole,
e. 4-methyl-5-[(2-aminoethyl)thiomethyl]oxazole,
f. 3-[(2-aminoethyl)thiomethyl]isoxazole,
g. 3-[(2-aminoethyl)thiomethyl]-1,2,4-triazole and
h. 2-[(2-aminoethyl)thiomethyl]-1,3,4-thiadiazole yielded the following products respectively:

a. 1-nitro-2-[2-((3-chloro-2-pyridyl)methylthio)ethylamino]-2-methylthioethylene,
b. 1-nitro-2-[2-((3-bromo-2-pyridyl)methylthio)ethylamino]-2-methylthioethylene,
c. 1-nitro-2-[2-((3-hydroxy-2-pyridyl)methylthio)ethylamino]-2-methylthioethylene,
d. 1-nitro-2-[2-(3-isothiazolylmethylthio)ethylamino]-2-methylthioethylene,
e. 1-nitro-2-[2-((4-methyl-5-oxazolyl)methylthio)ethylamino]-2-methylthioethylene,
f. 1-nitro-2-[2-(3-isoxazolylmethylthio)ethylamino]-2-methylthioethylene,
g. 1-nitro-2-[2-((3-(1,2,4-triazolyl)methylthio)ethylamino]-2-methylthioethylene and
h. 1-nitro-2-[2-((2-(1,3,4-thiadiazolyl)methylthio)ethylamino]-2-methylthioethylene.

EXAMPLE 11

A mixture of 1-nitro-2-methylthio-2-[2-(4-methyl-5-imidazolyl)methylthio)ethylamino]ethylene (0.67 g) and 33% ethanolic methylamine (4ml) was heated in a sealed tube at 70°–80° for 1 hour. Concentration, followed by purification of the product by chromatography on a column of silica gel with acetone as eluant and recrystallisation from acetonitrile furnished 1-nitro-2-methylamino-2-[2-((4-methyl-5-imidazolyl)methylthio)ethylamino]ethylene (0.39 g), m.p. 141°–3°. Further recrystallisation from isopropanol furnished a sample m.p. 148°–151°.

Found: C, 44.5; H, 6.6; N, 25.9; S, 11.4; $C_{10}H_{17}N_5O_2S$.

Requires: C, 44.3; H, 6.3; N, 25.8; S, 11.8.

We claim:

1. A process for the production of a compound of the formula:

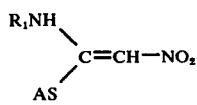

wherein A is lower alkyl; $R_1$ is lower alkyl, lower alkoxy, 2,2,2-trifluoroethyl, $(CH_2)_nR_2$ or $HetCH_2Z(CH_2)_2$; Het is an imidazole, thiazole, pyridine, isothiazole, oxazole, isoxazole, triazole or thiadiazole ring, which ring is optionally substituted by lower alkyl, hydroxyl, lower alkoxy, chlorine or bromine, Z is sulphur or methylene; $n$ is an integer from 1 to 12; and $R_2$ is hydroxy, lower alkoxy or lower alkylamino; wherein a compound of the formula:

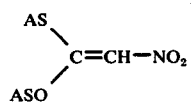

is reacted with an amine of formula $R_1NH_2$.

2. A process according to claim 1 wherein $R_1$ is $HetCH_2Z(CH_2)_2$ and Het is an imidazole, thiazole or pyridine ring, which ring is optionally substituted by methyl, hydroxy or chlorine.

3. A process according to claim 1 wherein $R_1$ is 2-[(5-methyl-4-imidazolyl)methylthio]ethyl.

4. A process according to claim 1 wherein $R_1$ is methyl.

* * * * *